United States Patent
Yamamoto et al.

(10) Patent No.: US 10,893,802 B2
(45) Date of Patent: Jan. 19, 2021

(54) INFORMATION PROCESSING APPARATUS, INFORMATION PROCESSING METHOD, AND RECORDING MEDIUM

(71) Applicant: SONY CORPORATION, Tokyo (JP)

(72) Inventors: Yuki Yamamoto, Chiba (JP); Eisuke Nomura, Tokyo (JP); Yoshiaki Iwai, Tokyo (JP); Takuro Noda, Tokyo (JP)

(73) Assignee: SONY CORPORATION, Tokyo (JP)

( * ) Notice: Subject to any disclaimer, the term of this patent is extended or adjusted under 35 U.S.C. 154(b) by 162 days.

(21) Appl. No.: 16/301,313

(22) PCT Filed: Mar. 22, 2017

(86) PCT No.: PCT/JP2017/011541
§ 371 (c)(1),
(2) Date: Nov. 13, 2018

(87) PCT Pub. No.: WO2017/203815
PCT Pub. Date: Nov. 30, 2017

(65) Prior Publication Data
US 2019/0191994 A1    Jun. 27, 2019

(30) Foreign Application Priority Data
May 27, 2016    (JP) .................................. 2016-105808

(51) Int. Cl.
*G06T 1/00*    (2006.01)
*A61B 3/113*    (2006.01)
(Continued)

(52) U.S. Cl.
CPC ................. *A61B 3/113* (2013.01); *A61B 3/14* (2013.01); *A61B 3/156* (2013.01); *G02B 27/02* (2013.01);
(Continued)

(58) Field of Classification Search
CPC ........... A61B 3/113; A61B 3/14; A61B 3/156; G02B 27/02; G02B 27/021; G06F 3/038;
(Continued)

(56) References Cited

U.S. PATENT DOCUMENTS 6,714,665 B1 *  3/2004  Hanna ...................... G06K 9/00
                                                    382/117
8,878,749 B1 * 11/2014  Wu .......................... G01S 17/06
                                                    345/8
(Continued)

FOREIGN PATENT DOCUMENTS

JP    H06-138379 A    5/1994
JP    H08-154899 A    6/1996
(Continued)

*Primary Examiner* — Sean T Motsinger
(74) *Attorney, Agent, or Firm* — Paratus Law Group, PLLC

(57) ABSTRACT

There is provided an information processing apparatus to make it possible to dynamically change the blinking pattern of the light source according to the imaging result, the information processing apparatus including: a light source control unit configured to control each of light sources constituting a plurality of light sources that irradiate an eye with light; and an image acquisition unit configured to acquire a captured image of the eye including a bright spot that is a reflection point of the light. The light source control unit controls blinking of each of the light sources on a basis of the captured image of the eye.

16 Claims, 12 Drawing Sheets

(51) Int. Cl.
  *G06F 3/038* (2013.01)
  *G02B 27/02* (2006.01)
  *A61B 3/15* (2006.01)
  *A61B 3/14* (2006.01)

(52) U.S. Cl.
  CPC .......... *G02B 27/021* (2013.01); *G06F 3/038* (2013.01); *G06T 1/00* (2013.01); *G06T 1/0007* (2013.01)

(58) Field of Classification Search
  CPC . G06F 3/011; G06F 3/013; G06T 1/00; G06T 1/0007
  See application file for complete search history.

(56) References Cited

U.S. PATENT DOCUMENTS

| | | | | |
|---|---|---|---|---|
| 8,971,570 | B1* | 3/2015 | Raffle | G06F 3/013 |
| | | | | 382/103 |
| 9,265,415 | B1* | 2/2016 | Starner | A61B 3/113 |
| 10,373,008 | B2* | 8/2019 | Ackerman | H04N 5/2329 |
| 2010/0245093 | A1* | 9/2010 | Kobetski | G06K 9/00597 |
| | | | | 340/576 |
| 2010/0253907 | A1* | 10/2010 | Korb | A61B 3/14 |
| | | | | 351/206 |
| 2011/0013007 | A1* | 1/2011 | Holmberg | G06K 9/00604 |
| | | | | 348/78 |
| 2011/0170061 | A1* | 7/2011 | Gordon | G06K 9/00604 |
| | | | | 351/206 |
| 2012/0105486 | A1* | 5/2012 | Lankford | G06F 3/0481 |
| | | | | 345/661 |
| 2012/0274775 | A1* | 11/2012 | Reiffel | G06Q 30/08 |
| | | | | 348/158 |
| 2014/0104574 | A1* | 4/2014 | Grenon | G06T 7/0012 |
| | | | | 351/206 |
| 2014/0313308 | A1* | 10/2014 | Wang | A61B 3/113 |
| | | | | 348/78 |
| 2015/0015478 | A1* | 1/2015 | Hoffman | G06F 3/013 |
| | | | | 345/156 |
| 2015/0097772 | A1* | 4/2015 | Starner | G06F 3/013 |
| | | | | 345/158 |
| 2015/0131051 | A1* | 5/2015 | Huang | A61B 3/0025 |
| | | | | 351/206 |
| 2015/0138504 | A1* | 5/2015 | Korb | G01B 11/06 |
| | | | | 351/206 |
| 2015/0138505 | A1* | 5/2015 | Grenon | A61B 3/0008 |
| | | | | 351/206 |
| 2015/0193920 | A1* | 7/2015 | Knee | H04N 5/23229 |
| | | | | 382/154 |
| 2015/0278576 | A1* | 10/2015 | Horesh | A61B 3/113 |
| | | | | 382/103 |
| 2016/0077337 | A1* | 3/2016 | Raffle | G02B 27/017 |
| | | | | 345/156 |
| 2016/0274659 | A1* | 9/2016 | Caraffi | G06F 3/013 |
| 2017/0031435 | A1* | 2/2017 | Raffle | G02B 27/017 |
| 2017/0280995 | A1* | 10/2017 | Yates | A61B 3/125 |
| 2017/0285741 | A1* | 10/2017 | Park | G06K 9/00617 |
| 2018/0239423 | A1* | 8/2018 | Mardanbegi | H04N 5/2354 |
| 2019/0158717 | A1* | 5/2019 | Nomura | H04N 5/2351 |
| 2019/0191994 | A1* | 6/2019 | Yamamoto | G06T 1/0007 |
| 2019/0317598 | A1* | 10/2019 | Aleem | G02B 27/0172 |
| 2019/0391040 | A2* | 12/2019 | Gamliel | G01M 11/025 |
| 2020/0072702 | A1* | 3/2020 | Gamliel | G01M 11/0278 |
| 2020/0154997 | A1* | 5/2020 | Noda | G06F 3/013 |

FOREIGN PATENT DOCUMENTS

| | | |
|---|---|---|
| JP | 2003-339642 A | 12/2003 |
| WO | WO 2013/175701 A1 | 11/2013 |

* cited by examiner

INFORMATION PROCESSING APPARATUS, INFORMATION PROCESSING METHOD, AND RECORDING MEDIUM

CROSS REFERENCE TO PRIOR APPLICATION

This application is a National Stage Patent Application of PCT International Patent Application No. PCT/JP2017/011541 (filed on Mar. 22, 2017) under 35 U.S.C. § 371, which claims priority to Japanese Patent Application No. 2016-105808 (filed on May 27, 2016), which are all hereby incorporated by reference in their entirety.

TECHNICAL FIELD

The present disclosure relates to an information processing apparatus, an information processing method, and a recording medium.

BACKGROUND ART

In recent years, along with the development of line-of-sight estimation techniques, research and development for improving the accuracy of the line-of-sight estimation have been performed. For example, Patent Literature 1 discloses a technique for improving an accuracy of a calculated pupil center point by devising a direction of light irradiated to an eyeball.

CITATION LIST

Patent Literature

Patent Literature 1: JP H6-138379A

DISCLOSURE OF INVENTION

Technical Problem

Here, a blinking pattern of a light source that irradiates the eyeball with light has a large influence on an accuracy of a line-of-sight estimation. In a case in which the blinking pattern of the light source is not able to be flexibly changed according to an imaging result, the accuracy of the line-of-sight estimation may decrease.

Therefore, the present disclosure is made in consideration of the above, and the present disclosure proposes new and improved information processing apparatus capable of dynamically changing a blinking pattern of a light source according to an imaging result.

Solution to Problem

According to the present disclosure, there is provided an information processing apparatus including: a light source control unit configured to control each of light sources constituting a plurality of light sources that irradiate an eye with light; and an image acquisition unit configured to acquire a captured image of the eye including a bright spot that is a reflection point of the light. The light source control unit controls blinking of each of the light sources on a basis of the captured image of the eye.

In addition, according to the present disclosure, there is provided a computer-readable recording medium having a program for realizing functions recorded thereon, the functions including: a light source control function of controlling each of light sources constituting a plurality of light sources that irradiate an eye with light; an image acquisition function of acquiring a captured image of the eve including a bright spot that is a reflection point of the light; and a function of controlling blinking of each of the light sources on a basis of the captured image of the eye.

In addition, according to the present disclosure, there is provided an information processing method including: controlling each of light sources constituting a plurality of light sources that irradiate an eye with light; and acquiring a captured image of the eye including a bright spot that is a reflection point of the light. Blinking of each of the light sources is controlled on a basis of the captured image of the eye.

Advantageous Effects of Invention

As described above, according to the present disclosure, it is possible to dynamically change the blinking pattern of the light source according to the imaging result.

Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
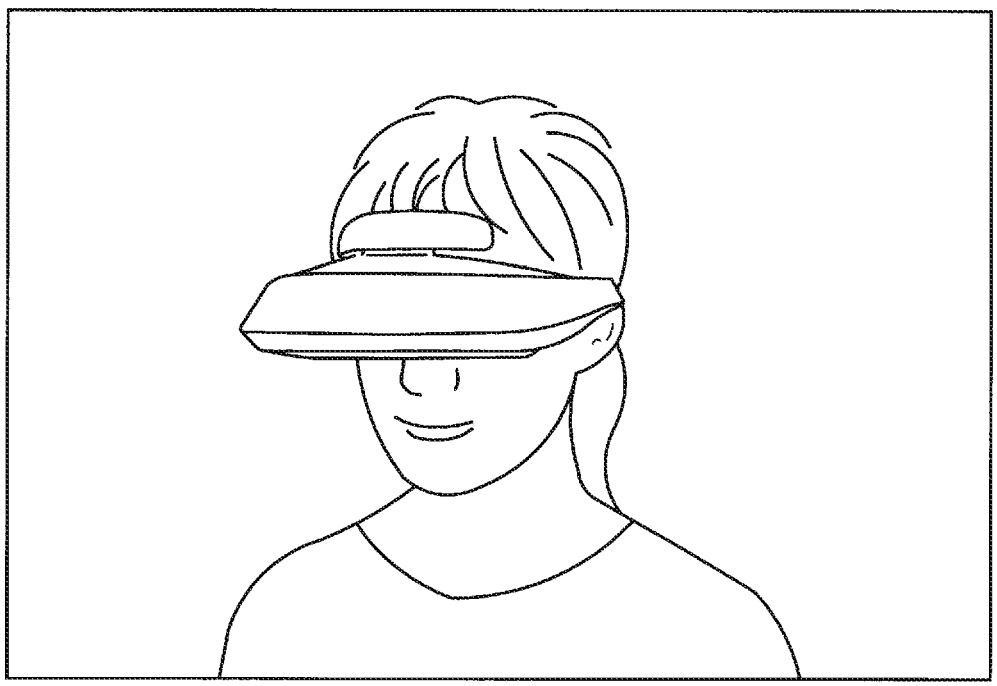
FIG. 1 is a schematic diagram of a head mounted display according to an embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

The description will be given in the following order.
1. Introduction
2. Embodiment of the present disclosure
2.1. Overview of embodiment of the present disclosure
2.2. Configuration of head mounted display
2.3. Operation of head mounted display
3. Change of blinking pattern of light source
3.1. Overview of change of blinking pattern of light source
3.2. Change of blinking pattern of light source based on pupil center position
3.3. Change of blinking pattern of light source based on distribution state of bright spot
3.4. Change of blinking pattern of light source based on eye related information
3.5. Change of blinking pattern of light source based on statistical information
3.6. Summary of embodiment of the present disclosure
4. Hardware configuration of head mounted display
5. Supplement <1. Introduction>

First, an overview of a line-of-sight estimation technique will be described. The line-of-sight estimation technique is a technique for estimating a line-of-sight by detecting a state of an eyeball including a position or movement of the eyeball. The line-of-sight estimation technique is able to be utilized for various purposes or products. For example, a layout of a product shelf can be improved by estimating a line-of-sight of a user with respect to a product displayed on the product shelf of a retail store and calculating the frequency or time at which the product is viewed. In addition, for example, the effect of an outdoor advertisement can be measured by estimating a line-of-sight of a user with respect to the outdoor advertisement and calculating the viewing frequency or time. In addition, a user can designate a point to be operated and operate a head mounted display without using a pointing device if a line-of-sight of a user with respect to a display of the head mounted display is estimated.

Along with dissemination of services or products utilizing such a line-of-sight estimation technique, development of sensing devices and imaging devices, or the like, and line-of-sight estimation techniques of various methods are being researched and developed. For example, a line-of-sight estimation technique of the following technique may be provided.

Pupil cornea reflex method: A technique in which a cornea is irradiated with light, a cornea curvature center point is calculated by associating a bright spot on the cornea with a light source, and a line-of-sight is estimated on the basis of the cornel curvature center point and a center point of a pupil.

Sclera reflection method: A technique in Which a boundary between the sclera and the cornea is irradiated with light and the line-of-sight is estimated on a basis of a difference in a reflection ratio between the sclera and the cornea.

Double Purkinje method: A technique in which the line-of-sight is estimated on a basis of a relative relationship between two reflected lights from a cornea surface and a back surface of a crystalline lens.

Image processing method: A technique in which the line-of-sight is estimated by performing some kind of imaging processing on a captured image of an eyeball.

Search coil method: A technique in which a special contact lens provided with a coil is attached to the eyeball, an eye movement is measured by a principle of electromagnetic induction, and thus the line-of-sight is estimated.

Electro oculography (EOG) method: A technique in which the line-of-sight is estimated on a basis of a change in a potential by a rotation of the eyeball.

<2. Embodiment of the Present Disclosure>

[2.1. Overview of Embodiment of the Present Disclosure]

In an embodiment of the present disclosure, a head mounted display in which a line-of-sight estimation is performed by using the pupil cornea reflex method among. the line-of-sight estimation technologies described above will be described.

First, an overview of the head mounted display 100 according to an embodiment of the present disclosure will be described with reference to FIG. 1. FIG. 1 is a schematic diagram of the head mounted display 100 according to an embodiment of the present disclosure. As shown in FIG. 1, the head mounted display 100 according to an embodiment of the present disclosure is an information processing apparatus that is attached to a head of a user and a generated image is displayed on a display in front of the user's eyes. The head mounted display shown in FIG. 1 is a shield type head mounted display in which the entire view of a wearer is covered, but an arbitrary type may be applied to a head mounted display capable of performing the line-of-sight estimation by the pupil cornea reflex method. For example, the head mounted display 100 according to an embodiment of the present disclosure may be an open type head mounted display in which the entire view of the wearer is not covered.

Figure 2:
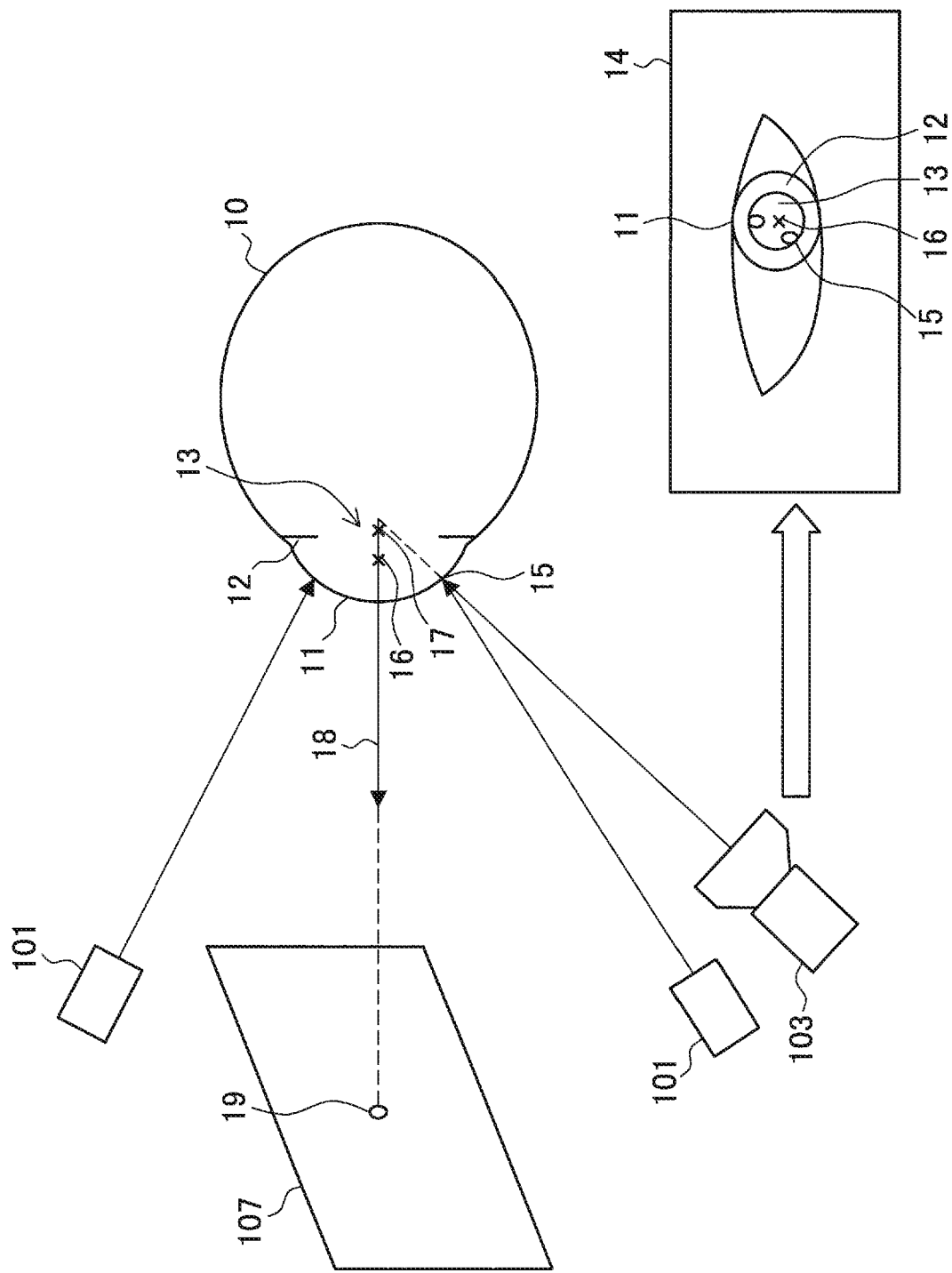
FIG. 2 is a schematic diagram of line-of-sight estimation by the head mounted display according to an embodiment of the present disclosure.

Next, an overview of the line-of-sight estimation technique using the head mounted display 100 according to an embodiment of the present disclosure will be described with reference to FIG. 2. FIG. 2 is a schematic diagram of line-of-sight estimation by the head mounted display according to an embodiment of the present disclosure. FIG. 2 shows a plurality of light sources 101, an imaging unit 103, and a display unit 107 that are parts of configuration elements of the head mounted display 100, and an eyeball 10 on which the line-of-sight estimation is performed. Although only two light sources 101 are shown in FIG. 2, any number of light sources 101 may be provided as long as a plurality of light sources 101 are provided. In addition, FIG. 2 also schematically shows a captured image 14 captured by the imaging unit 103. Further, FIG. 2 also schematically shows a cornea 11, an iris 12, and a pupil 13 of the eyeball 10, and the shape of the eyeball 10 is approximated by two different spherical surfaces of a spherical surface of a portion of the cornea 11 and a main body of the eyeball 10.

In the line-of-sight estimation by the head mounted display 100 according to an embodiment of the present disclosure, the eyeball 10 is irradiated with light from the plurality of light sources 101 and the imaging unit 103 images the eyeball 10. In the captured image 14 captured by the imaging unit 103, a bright spot 15 (also referred to as a Purkinje image) that is a reflection point of the light or the pupil 13 is imaged on the cornea 11.

Subsequently, the plurality of light sources 101 and the bright spot 15 generated by light emitted from the light source 101 and reflected on the cornea are associated with each other. A cornea curvature center point 17 is calculated on the basis of the association. A method of calculating the cornea curvature center point 17 will be described later. In addition, a pupil center point 16 is calculated by analyzing the pupil 13 imaged by the imaging unit 103. A method of calculating the pupil center point 16 will be described later. In addition, an optical axis that is a vector directed from the calculated cornea curvature center point 17 to the pupil center point 16 is obtained. Next, a visual axis 18 that is the line-of-sight of the user is obtained by suitably correcting the optical axis. A method of correcting the optical axis will be described later. Next, coordinates of a line-of-sight estimation point 19 at which the visual axis 18 and the display unit 107 intersect with each other are calculated on a basis of a positional relationship between the display unit 107 and the eyeball 10 in a three-dimensional space. Details of the line-of-sight estimation method will be described later.

[2.2. Configuration of Head Mounted Display]

Figure 3:
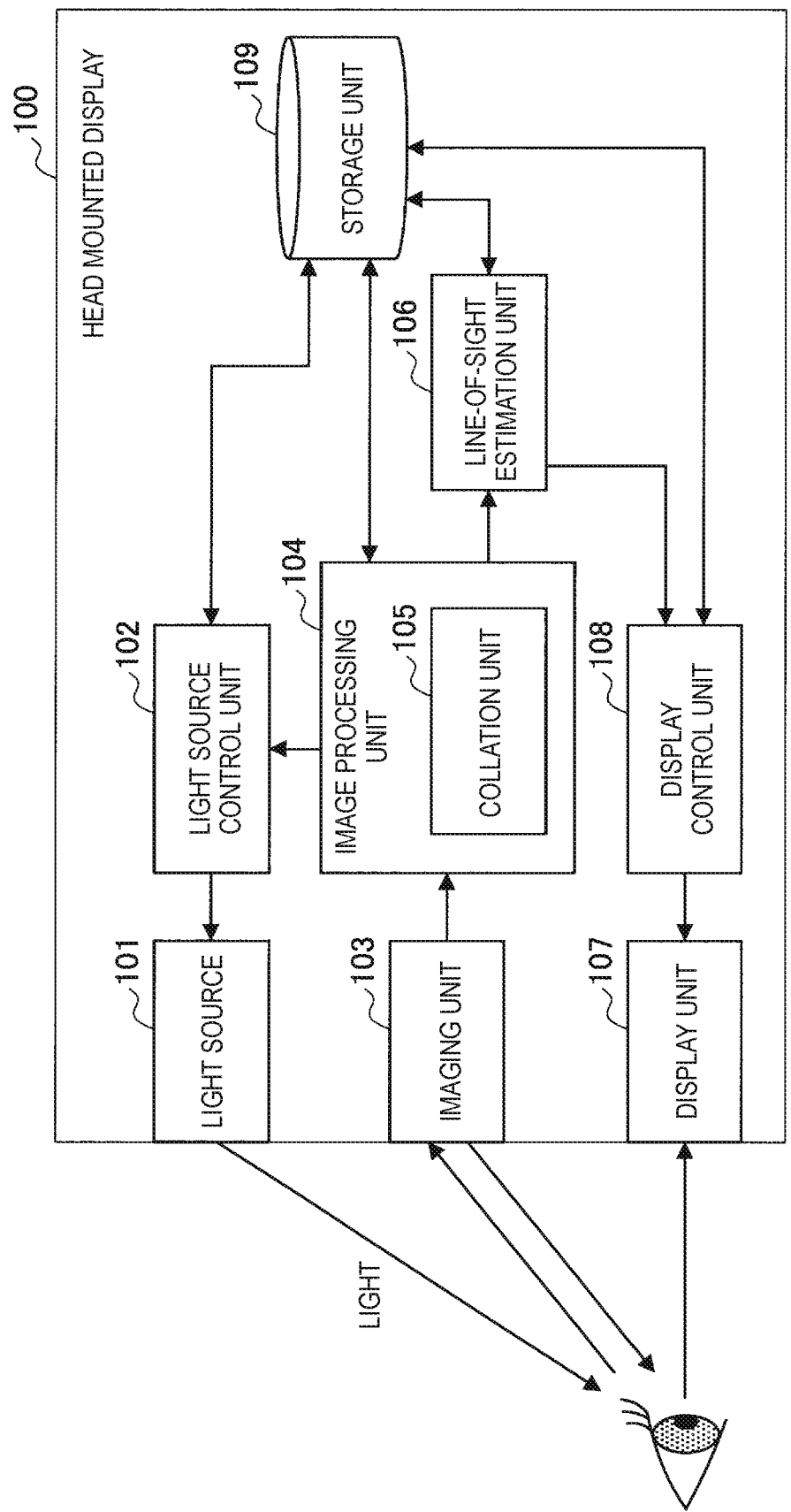
FIG. 3 is a block diagram illustrating a configuration of the head mounted display according to an embodiment of the present disclosure.

The overview of the line-of-sight estimation technique using the head mounted display 100 according to an embodiment of the present disclosure has been described above. Next, the configuration of the head mounted display 100 according to an embodiment of the present disclosure will be described with reference to FIG. 3. FIG. 3 is a block diagram illustrating the configuration of the head mounted display 100 according to an embodiment of the present disclosure. The head mounted display includes a light source 101, a light source control unit 102, an imaging unit 103, an image processing unit 104, a collation unit 105, a line-of-sight estimation unit 106, a display unit 107, a display control unit 108, and a storage unit 109. The collation unit 105 is one module of the image processing unit 104. A plurality of light sources 101 are provided.

The light source 101 irradiates the eyeball 10 with light. Specifically, the light source 101 is switched between an on state and an off state under control of the light source control unit 102, and the light source 101 in the on state irradiates the eyeball 10 with the light. In the head mounted display 100 according to an embodiment of the present disclosure, the plurality of light sources 101 are provided at different positions, and each light source 101 irradiates the eyeball 10 with the light. Therefore, a plurality of bright spots 15 are generated on the cornea.

The imaging unit 103 functions as an image acquisition unit, images the bright spot 15 or an eye including the eyeball 10, an outer corner of the eye, an inner corner of the eye, an eyelid, an eyelash, and the like of the user, and generates captured image information. Specifically, the imaging unit 103 is provided at a position where it is possible to image an eye movement, the bright spot 15, and the like, and generates the captured image information corresponding to the captured image. Note that the imaging unit 103 images one eye or both eyes of the user. In addition, the imaging unit 103 provides the captured image information to the image processing unit 104.

The image processing unit 104 analyzes the captured image information provided from the imaging unit 103 and generates imaging analysis information. Specifically, the image processing unit 104 detects the bright spot 15 or the pupil 13 by analyzing the captured image information and generates imaging analysis information including information regarding a position of the bright spot 15 (hereinafter, referred to as "bright spot related information") and imaging analysis information including information regarding a position of the pupil 13 (hereinafter, referred to as "pupil related information"). Details of a method of detecting the bright spot 15 or the pupil 13 will be described later.

In addition, the image processing unit 104 generates imaging analysis information including information regarding the eye (the outer corner of the eye, the inner corner of the eye, the eyelid, the eyelash, and the like) (hereinafter, referred to as "eye related information") by analyzing the captured image information. For example, the image processing unit 104 generates eye related information including the presence or absence of eye opening or closing (blinking or the like) or an opening or closing speed of the eye by analyzing a state of the outer corner of the eye, the inner corner of the eye, the eyelid, the eyelash, and the like. In addition, the image processing unit 104 generates eye related information including a position of the eyelash or the like. These are examples of the eye related information and the eye related information is arbitrary as long as the eye related information is information regarding the state of the eye.

Next, the image processing unit 104 provides the above-described bright spot related information to the light source control unit 102, the collation unit 105, and the line-of-sight estimation unit 106. The provided bright spot related information is used in changing the blinking pattern of the light source 101 by the light source control unit 102, associating the bright spot 15 and the light source 101 with each other by the collation unit 105, and estimating the optical axis by the line-of-sight estimation unit 106.

In addition, the image processing unit 104 provides the above-described pupil related information to the light source control unit 102 and the line-of-sight estimation unit 106. The provided pupil related information is used in determining a state (any of an on state and an off state) of the light source 101 by the light source control unit 102 and estimating the optical axis by the line-of-sight estimation unit 106.

In addition, the image processing unit 104 provides the above-described eye related information to the light source control unit 102. The provided eye related information is used in determining the state (any of the on state and the off state) of the light source 101 by the light source control unit 102.

The collation unit 105 associates the light source 101 with the bright spot 15 generated by the light radiated from the light source 101. Specifically, the collation unit 105 associates the light source 101 with the bright spot 15 on a basis of the bright spot related information provided from the image processing unit 104 and a blinking pattern of the plurality of light sources 101 provided from the light source control unit 102. In addition, the collation unit 105 generates bright spot light source correspondence information in which identification information such as an ID is given to the information in which the light source 101 and the bright spot 15 are associated with each other. A method of associating the light source 101 and the bright spot 15 with each other will be described later.

In addition, the collation unit 105 provides the bright spot light source correspondence information to the light source control unit 102 and the line-of-sight estimation unit 106. The provided bright spot light source correspondence information is used in determining the state (any of the one state or the off state) of the light source 101 by the light source control unit 102 and estimating the optical axis by the line-of-sight estimation unit 106.

The line-of-sight estimation unit 106 estimates the line-of-sight on the basis of various pieces of information. Specifically, the line-of-sight estimation unit 106 estimates the optical axis on the basis of the bright spot related information and the pupil related information provided from the image processing unit 104 and the bright spot light source correspondence information provided from the collation unit 105. In addition, the line-of-sight estimation unit 106 estimates the visual axis 18 that is the line-of-sight of the user by correcting the optical axis, generates line-of-sight estimation information including information related to the visual axis 18, and provides the line-of-sight estimation information to the display control unit 108. The provided line-of-sight estimation information is used for controlling the display unit 107 by the display control unit 108.

The display unit 107 displays various pieces of information. Specifically, the display unit 107 visually notifies the user of the various pieces of the information by displaying the various pieces of information in various formats such as an image, text, and a graph, under control of the display control unit 108. Various types of content may be included in the various pieces of the information. In addition, the display unit 107 displays a line-of-sight estimation point 19 of the user under the control of the display control unit 108.

The display control unit 108 controls the display unit 107. Specifically, the display control unit 108 determines content of the information to be displayed on the display unit 107 on the basis of processing of an activated application and displays the information on the display unit 107. In addition, the display control unit 108 calculates the coordinates of the line-of-sight estimation point 19 at which the visual axis 18 and the display unit 107 intersect with each other on the basis of the line-of-sight estimation information provided from the line-of-sight estimation unit 106 and displays a point at the coordinates on the display unit 107.

The light source control unit 102 controls the blinking of each of the plurality of light sources 101. Specifically, the light source control unit 102 sets the state of each light source 101 in each frame to the on state or the off state on the basis of the blinking pattern that is the information regarding the on or off state of the plurality of light sources 101 in each frame. In addition, the light source control unit 102 controls the blinking of each of the plurality of light sources 101. Specifically, the light source control unit 102 is able to determine the state (any of the on state or the off state) of each light source 101 and suitably change the blinking pattern on the basis of the bright spot related information, the pupil related information, and the eye related information provided from the image processing unit 104 and the bright spot light source correspondence information provided from the collation unit 105. A method of changing the blinking pattern will be described later. In addition, the light source control unit 102 provides the blinking pattern to the collation unit 105. The provided blinking pattern is used in associating the bright spot 15 and the light source 101 with each other by the collation unit 105.

The storage unit 109 stores various pieces of information used for the line-of-sight estimation, the light source control, the display control, or the like. Specifically, the storage unit 109 may acquire and store the captured image information, the bright spot related information, the pupil related information, the eye related information, the bright spot light source correspondence information, the line-of-sight estimation information, and the blinking pattern described above. In addition, the storage unit 109 stores various parameters used in the line-of-sight estimation, content information displayed on the display unit 107, and the like.

[2.3. Operation of Head Mounted Display]

Figure 4:
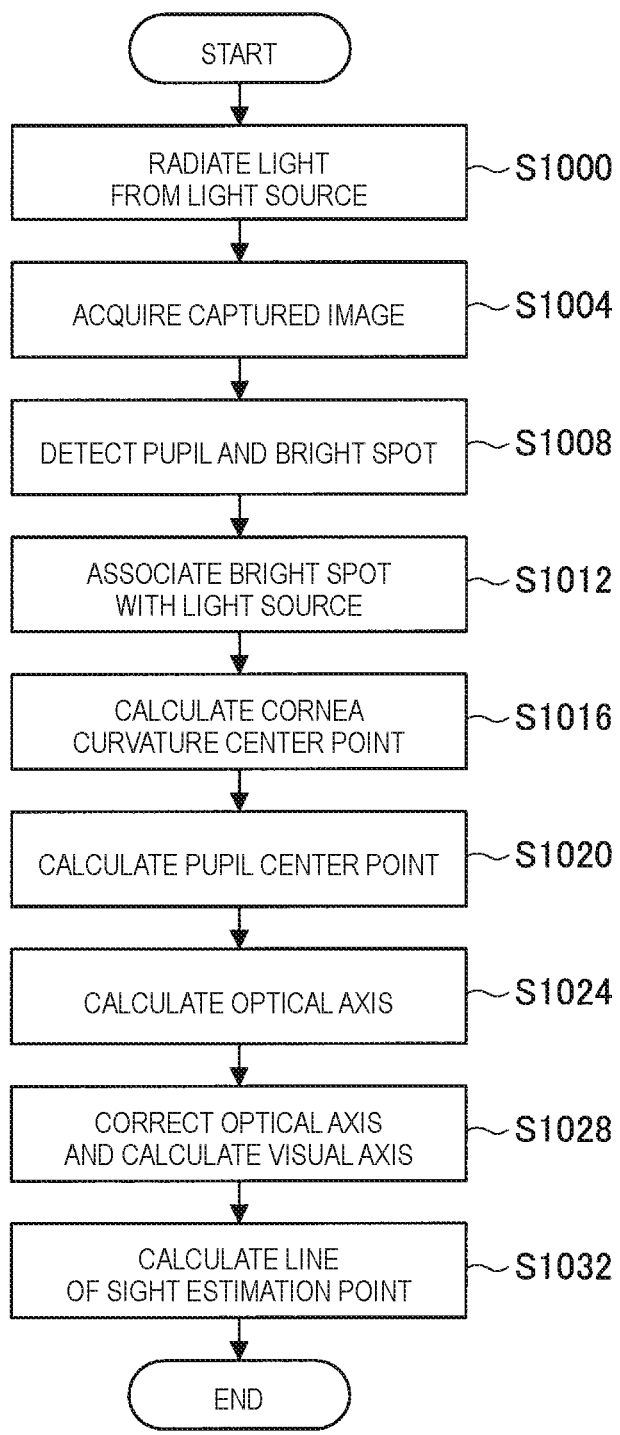
FIG. 4 is a flowchart illustrating an operation of the head mounted display according to an embodiment of the present disclosure.

The configuration of the head mounted display 100 has been described above. Subsequently, the operation of the head mounted display 100 will be described with reference to FIG. 4. FIG. 4 is a flowchart illustrating the operation of the head mounted display 100 according to an embodiment of the present disclosure.

First, the light source control unit 102 turns on and off the plurality of light sources 101 according to the blinking pattern of the light source 101 set in advance, and thus the eye is irradiated with the light from the light source 101 (step S1000). Therefore, the plurality of bright spots 15 are generated on the cornea.

Next, the imaging unit 103 images a state of the eye (step S1004). Therefore, the captured image information obtained by imaging the bright spot 15 generated on the cornea, the pupil 13, and the like is generated. The imaging unit 103 provides the captured image information to the image processing unit 104.

In addition, the image processing unit 104 analyzes the captured image information provided from the imaging unit 103 and detects the bright spot 15 and the pupil 13 (step S1008). A machine learning technique may be used in detecting the bright spot 15. Specifically, a machine learning program constructed in advance reads and learns about tens to tens of thousands of captured images obtained by imaging the bright spot. The image processing unit 104 may detect the bright spot 15 included in the captured image using the program.

In addition, a publicly known image recognition technique other than the machine learning is also able to be used in the detection processing of the bright spot 15. For example, the image processing unit 104 may perform a series of processes such as various kinds of image processing on the captured image, processing of acquiring a luminance distribution in the captured image, and processing of detecting a pixel having a relatively large difference in a luminance value with a surrounding pixel on the basis of the luminance distribution. In addition, the image processing unit 104 provides the generated bright spot related information to the light source control unit 102, the collation unit 105, and the line-of-sight estimation unit 106.

On the other hand, similarly to the detection processing of the bright spot 15, even in the detection processing of the pupil 13, the machine learning technique may be used and a publicly known image recognition technique other than the machine learning may be used. For example, the image processing unit 104 may perform a series of processes such as various kinds of image processing (adjustment processing of distortion, a black level, a white balance, or the like) on the captured image, processing of acquiring a luminance distribution in the captured image, processing of acquiring an outline (an edge) of the pupil 13 on the basis of the luminance distribution, and processing of approximating the detected outline of the pupil 13 with a figure such as a circle or an ellipse. In addition, the image processing unit 104 provides the generated pupil related information to the light source control unit 102 and the line-of-sight estimation unit 106.

Next, the collation unit 105 associates the bright spot 15 and the light source 101 with each other (step S1012). Specifically, the collation unit 105 acquires the bright spot related information from the image processing unit 104 and acquires the blinking pattern of the light source 101 from the light source control unit 102. The bright spot related information includes information related to the position where the bright spot 15 is generated and the frame when the bright spot 15 is generated, and the blinking pattern includes information related to the state (the on state or the off state) of the light source 101 in each frame. The collation unit 105 associates the bright spot 15 and the light source 101 with each other on a basis of a physical position relationship between the bright spot 15 and the light source 101. For example, a bright spot 15 closest to a certain light source 101 among the bright spots 15 generated on the cornea is set as the bright spot 15 corresponding to the light source 101. Here, the association method described above is an example, and the association between the bright spot 15 and the light source 101 may be performed by another method. For example, the collation unit 105 may associate the bright spot 15 and the light source 101 with each other using a machine learning program that has learned a correspondence relationship between the light source 101 and the bright spot 15 in advance.

Next, the line-of-sight estimation unit 106 calculates three-dimensional coordinates of the cornea curvature center point 17 (in a case in which the cornea is regarded as a part of a sphere, a center of the sphere) on the basis of the bright spot related information provided from the image processing unit 104 and the bright spot light source correspondence information provided from the collation unit 105 (step S1016). Specifically, the line-of-sight estimation unit 106 calculates the three-dimensional coordinates of the cornea curvature center point 17 of the cornea by solving a geometric calculation formula on a basis of a three-dimensional positional relationship of the imaging unit 103, the light source 101, and the bright spot 15 corresponding to the light source 101.

Next, the line-of-sight estimation unit 106 calculates three-dimensional coordinates of the pupil center point 16 on the basis of the pupil related information provided from the image processing unit 104 (step S1020). Specifically, the line-of-sight estimation unit 106 calculates three-dimensional coordinates of a plurality of points on the outline of the pupil 13 in the captured image by using parameters of a positional relationship between the imaging unit 103 and the eyeball 10, a refractive index of light on a cornea surface, a distance between the cornea curvature center point 17 of the cornea and the pupil center point 16, and the like, and obtains center points of such coordinates to calculate the three-dimensional coordinates of the pupil center point 16.

Next, the line-of-sight estimation unit 106 obtains the optical axis (the direction in which the eyeball 10 is facing), by calculating the vector directed from the three-dimensional coordinates of the cornea curvature center point 17 calculated in step S1016 to the three-dimensional coordinates of the pupil center point 16 calculated in step S1020 (step S1024).

Here, in humans, the optical axis does not always coincide with a direction in which the line-of-sight is actually directed by a human (hereinafter, referred to as a visual axis). This is caused by a shape and a size of the eyeball 10, a disposition of a retina or an optic nerve in the eyeball 10, and the like, and has individual differences. As described above, there is an error peculiar to the user between the optical axis and the visual axis.

In consideration of such circumstances, in an embodiment of the present disclosure, the line-of-sight estimation unit 106 performs processing of correcting the optical axis to the visual axis 18 (step S1028). For example, information related to a correlation between a gaze point and the optical axis when the line-of-sight is directed to the gaze point is acquired in advance by presenting the gaze point to the user, and the line-of-sight estimation unit 106 is able to acquire the visual axis 18 by correcting the optical axis on the basis of the corresponding information. However, since this correction method is an example, the line-of-sight estimation unit 106 is able to adopt an arbitrary correction method.

Next, the line-of-sight estimation unit 106 calculates the line-of-sight estimation point 19 of the user on the basis of the visual axis 18 (step S1032). Specifically, the line-of-sight estimation unit 106 ascertains the coordinates of the display unit 107 in the camera coordinate system as setting information (parameters or the like). Therefore, the line-of-sight estimation unit 106 is able to calculate the coordinates that are an intersection of the display unit 107 and the visual axis 18 in the camera coordinate system. These coordinates are the line-of-sight estimation point 19 estimated as the gaze point of the user.

The line-of-sight estimation of the user is performed using the head mounted display 100 according to an embodiment of the present disclosure, by performing the processing described above.

<3. Change of Blinking Pattern of Light Source>

[3.1. Overview of Change of Blinking Pattern of Light Source]

Figure 5:
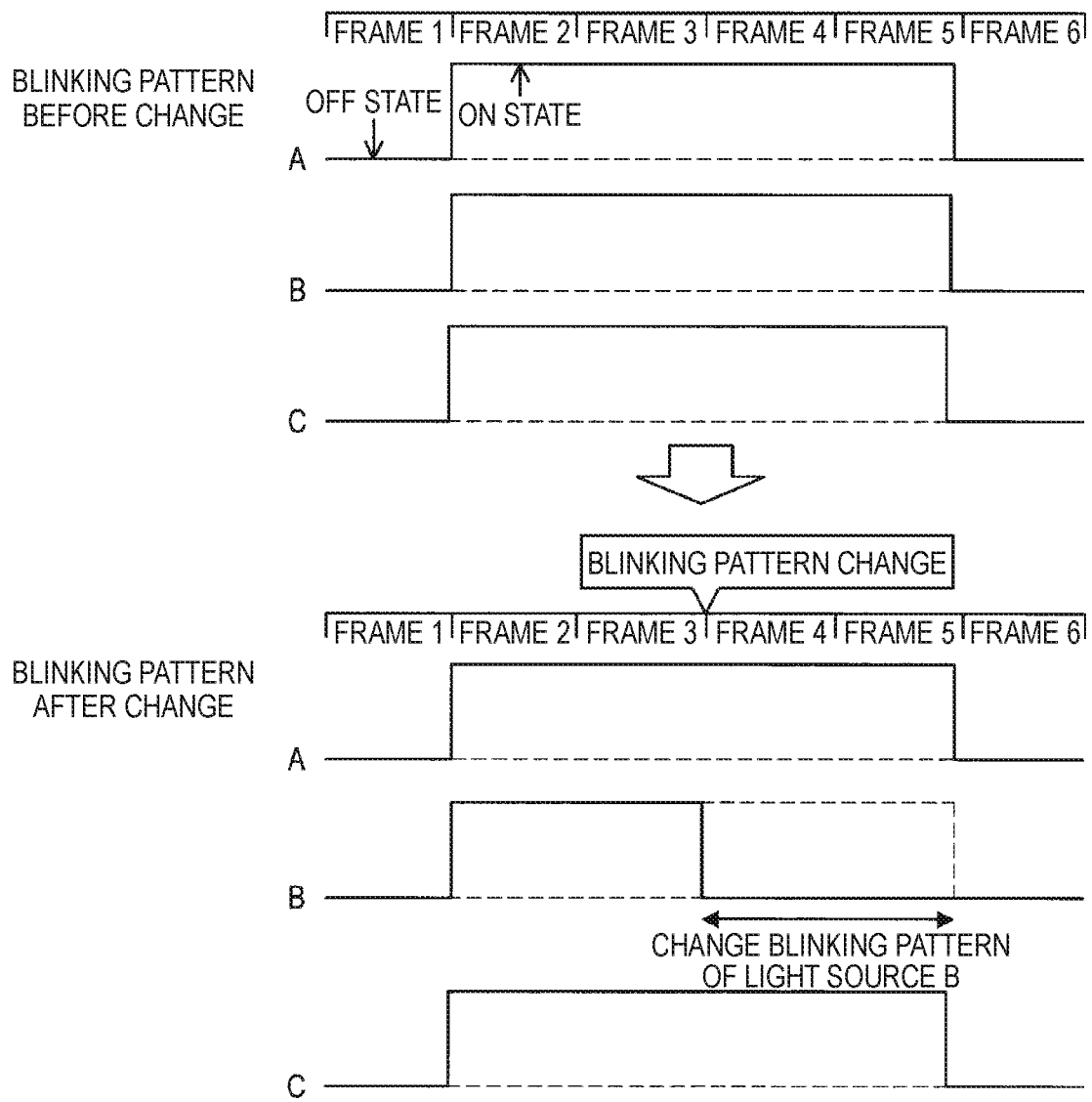
FIG. 5 is a schematic diagram illustrating a change example of a blinking pattern of a light source according to an embodiment of the present disclosure.

The operation of the head mounted display 100 according to an embodiment of the present disclosure has been described above. Subsequently, processing in which the light source control unit 102 changes the blinking pattern of the light source 101 on the basis of the imaging analysis information provided from the image processing unit 104 will be described with reference to FIG. 5. FIG. 5 is a schematic diagram illustrating a change example of the blinking pattern of the light source 101 according to an embodiment of the present disclosure. In addition, in the following description, a frame in which the imaging processing is performed by the imaging unit 103 will be referred to as a "current frame" and a frame in which the imaging processing is performed next to the current frame will be referred to as a "next frame".

First, the light source control unit 102 controls the blinking of each of the plurality of light sources 101 on the basis of the "blinking pattern before change" shown in FIG. 5. In addition, the light source control unit 102 acquires the imaging analysis information for each frame generated by the image processing unit 104 and determines the state (any of the on state or the off state) of the light source 101 in the next and subsequent frames on the basis of the imaging analysis information. If, in a case in which the state of the light source 101 in the next and subsequent frames is different from the state determined as described above, in the used blinking pattern, the light source control unit 102 changes the blinking pattern.

For example, in FIG. 5, it is assumed that the light source control unit 102 determines light sources A and C as the light sources 101 to be in the on state in frames 4 and 5 on the basis of the imaging analysis information obtained before a frame 3. In the blinking pattern before the change, since the state of the light source B is in the on state in the frames 4 and 5, the light source control unit 102 changes the blinking pattern to the blinking pattern in which the state of the light source B is in the off state in the frames 4 and 5. In the above-described example, the light source control unit 102 determines the state of the light source 101 in the next and subsequent frames, but the light source control unit 102 may determine the state of the light source 101 only in the next frame.

[3.2. Change of Blinking Pattern of Light Source Based on Pupil Center Position]

Figure 6:
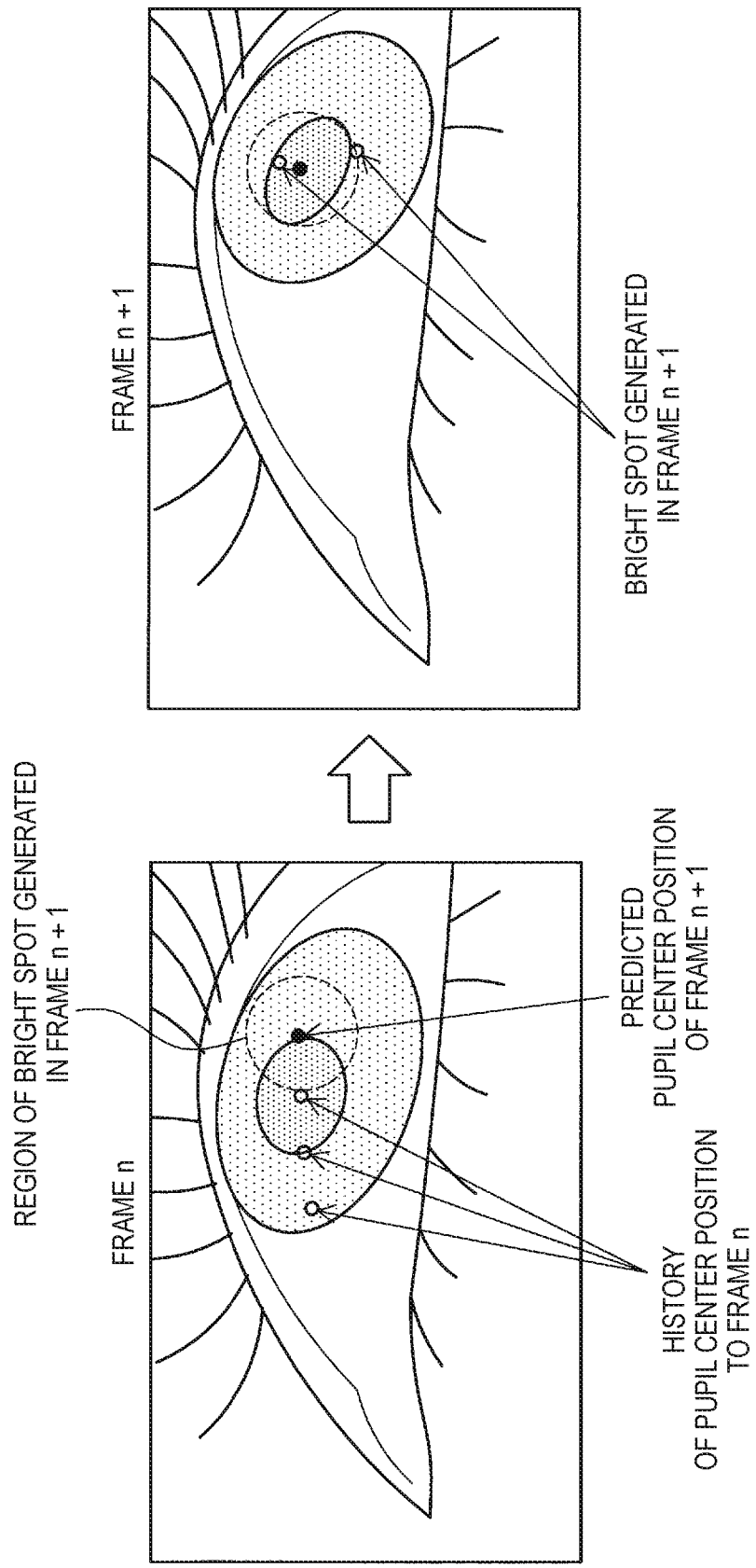
FIG. 6 is a schematic diagram illustrating a change example of the blinking pattern of the light source based on a pupil center position according to an embodiment of the present disclosure.

Subsequently, an overview of the change of the blinking pattern of the light source 101 based on the pupil center position will be described with reference to FIG. 6. FIG. 6 is a schematic diagram illustrating a change example of the blinking pattern of the light source 101 based on the pupil center position according to an embodiment of the present disclosure.

This method is a method of changing the blinking pattern so that the bright spot 15 is generated at the position relatively close to the pupil center position. It is assumed that the pupil center position is a center position of a circle or an ellipse in a case in which the pupil is approximated to the circle or the ellipse in a two-dimensional captured image. Here, the pupil center position may be the position of the intersection of the optical axis and the cornea 11 described above. Detection processing of the pupil center position will be described later.

First, as shown in FIG. 6, the pupil center position in a frame n is detected. In addition, the pupil center position in a frame n+1 is predicted on the basis of the pupil center position and the pupil center position in a frame imaged before the frame n. In addition, in the frame n+1, the blinking pattern of the light source 101 is changed so as to generate a predetermined number of bright spots 15 relatively close to the predicted pupil center position.

Figure 7:
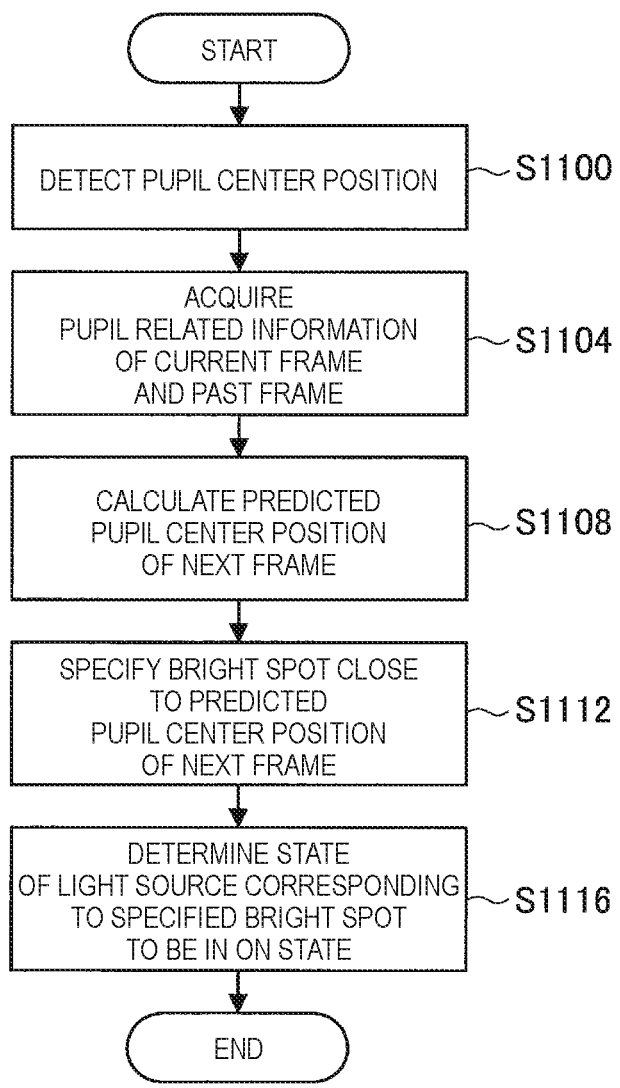
FIG. 7 is a flowchart illustrating change processing of the blinking pattern of the light source based on the pupil center position according to an embodiment of the present disclosure.

Next, a processing flow related to the change of the blinking pattern of the light source 101 based on the pupil center position will be described with reference to FIG. 7. FIG. 7 is a flowchart illustrating the change processing of the blinking pattern of the light source 101 based on the pupil center position according to an embodiment of the present disclosure.

First, the image processing unit 104 analyzes the captured image information provided from the imaging unit 103 and detects the pupil center position (step S1100). For example, the detection processing of the pupil center position may be a series of processes such as image processing (for example, adjustment processing of distortion, a black level, a white balance, or the like) on the captured image, processing of acquiring a luminance distribution in the captured image, processing of detecting an outline (an edge) of the pupil 13 on the basis of the luminance distribution, processing of approximating the detected outline of the pupil 13 to a figure such as a circle or an ellipse, and processing of calculating the center position of the approximate circle or the ellipse.

Next, the light source control unit 102 acquires the pupil related information including the information regarding the pupil center position in the current frame and a past frame generated by the image processing unit 104 (step S1104). In addition, the light source control unit 102 calculates the predicted pupil center position in the next frame on the basis of the pupil related information (step S1108). For example, the light source control unit 102 calculates the predicted pupil center position in the next frame by applying three-dimensional coordinate information of the pupil center position included in the pupil related information to a polynomial function.

Next, the light source control unit 102 specifies the predetermined number of bright spots 15 relatively close to the predicted pupil center position in the next frame among the bright spots 15 included in the bright spot light source correspondence information provided from the collation unit 105 (step S1112). At this time, any number of bright spots 15 may be specified. In addition, the light source control unit 102 determines the state of the light source 101 corresponding to the specified bright spot 15 to be in the on state in the next frame (step S1116). Here, in a case in which the blinking pattern used by the light source control unit 102 does not set the state of the light source 101 to be in the on state in the next frame, the light source control unit 102 changes the blinking pattern to the blinking pattern that sets the state of the specified light source 101 to be the on state in the next frame.

In a case in which the shape of the eyeball 10 is approximated to the two different spherical surfaces of the spherical surface of the portion of the cornea 11 and the main body of the eyeball 10 as in an embodiment of the present disclosure, the line-of-sight estimation performed on the basis of the bright spot 15 generated at a position closer to the pupil center position is more accurate. Therefore, according to the method described above, it is possible to improve the accuracy of the line-of-sight estimation. In addition, since the light source 101 that is set to be in the on state is limited, it is easy to associate the bright spot 15 and the light source 101 with each other. Therefore, since it is possible to decrease an error in associating the bright spot 15 and the light source 101 with each other, it is possible to improve the accuracy of the line-of-sight estimation.

[3.3. Change of Blinking Pattern of Light Source Based on Distribution State of Bright Spot]

Figure 8:
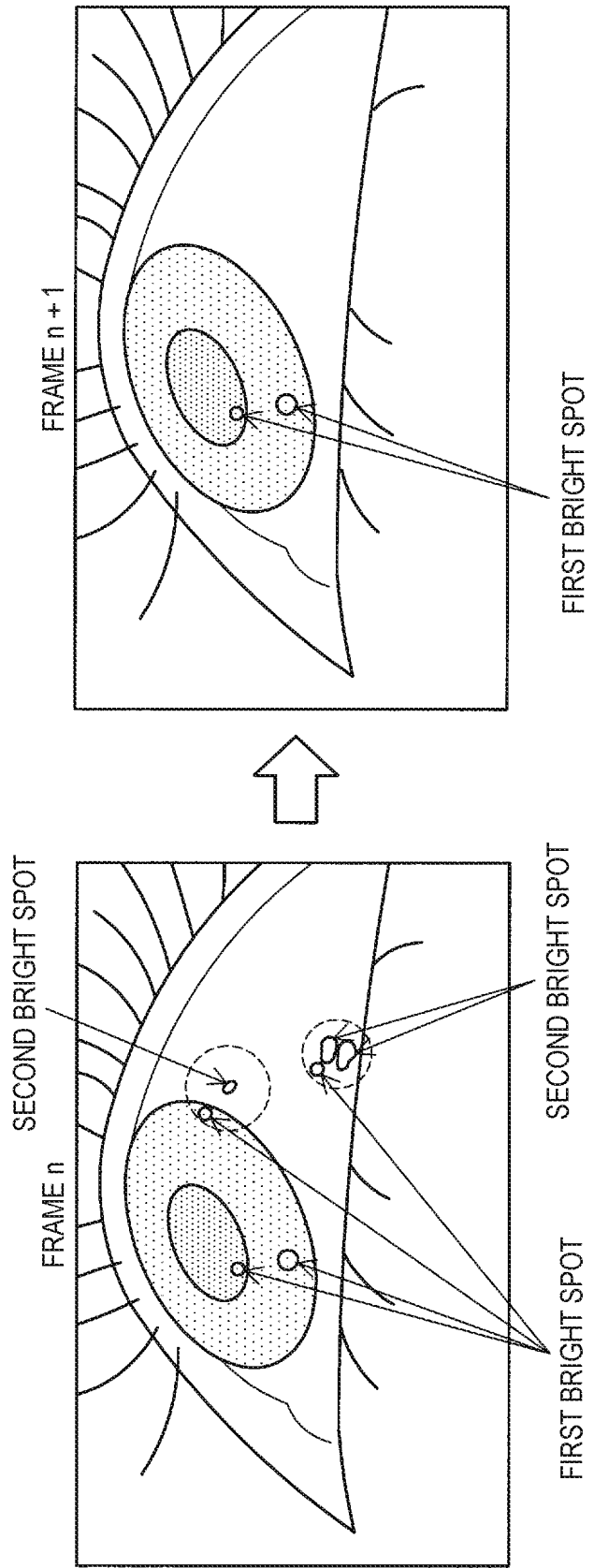
FIG. 8 is a schematic diagram illustrating a change example of the blinking pattern of the light source based on a distribution state of bright spots according to an embodiment of the present disclosure.

The change of the blinking pattern of the light source 101 based on the pupil center position has been described above. Subsequently, the change of the blinking pattern of the light source 101 based on the distribution state of the bright spots 15 will be described with reference to FIG. 8. FIG. 8 is a schematic diagram illustrating a change example of the blinking pattern of the light source 101 based on the distribution state of the bright spots 15 according to an embodiment of the present disclosure.

This method is a method of changing the blinking pattern so as not to generate the bright spots 15 that are in the distribution state. The distribution state refers to the bright spot 15 that is not able to be associated with the light source 101. For example, as shown in the captured image of the frame n of FIG. 8, the light radiated from the light source 101 is dispersed due to the positional relationship between the light source 101 and the eyeball 10 or an influence of a shield such as the eyelid or the eyelash and a plurality of bright spots 15 corresponding to the light are generated in some cases. In addition, outside light is imaged as the bright spot 15 due to an influence of ambient light in some cases. As described above, in a case in which the plurality of bright spots 15 are generated corresponding to one light source 101, the association with the light source 101 fails. As described above, this method is a method of changing the blinking pattern so as not to generate the bright spot 15 that is not able to be associated with the light source 101.

Specifically, as shown in FIG. 8, the bright spot 15 is detected in the frame n, and the light source 101 and the bright point 15 are associated with each other. Then, when the bright spot 15 without a corresponding light source 101 is detected, the blinking pattern of the light source 101 is changed in the frame n+1 so that this bright spot 15 does not occur in the frame n+1.

Figure 9:
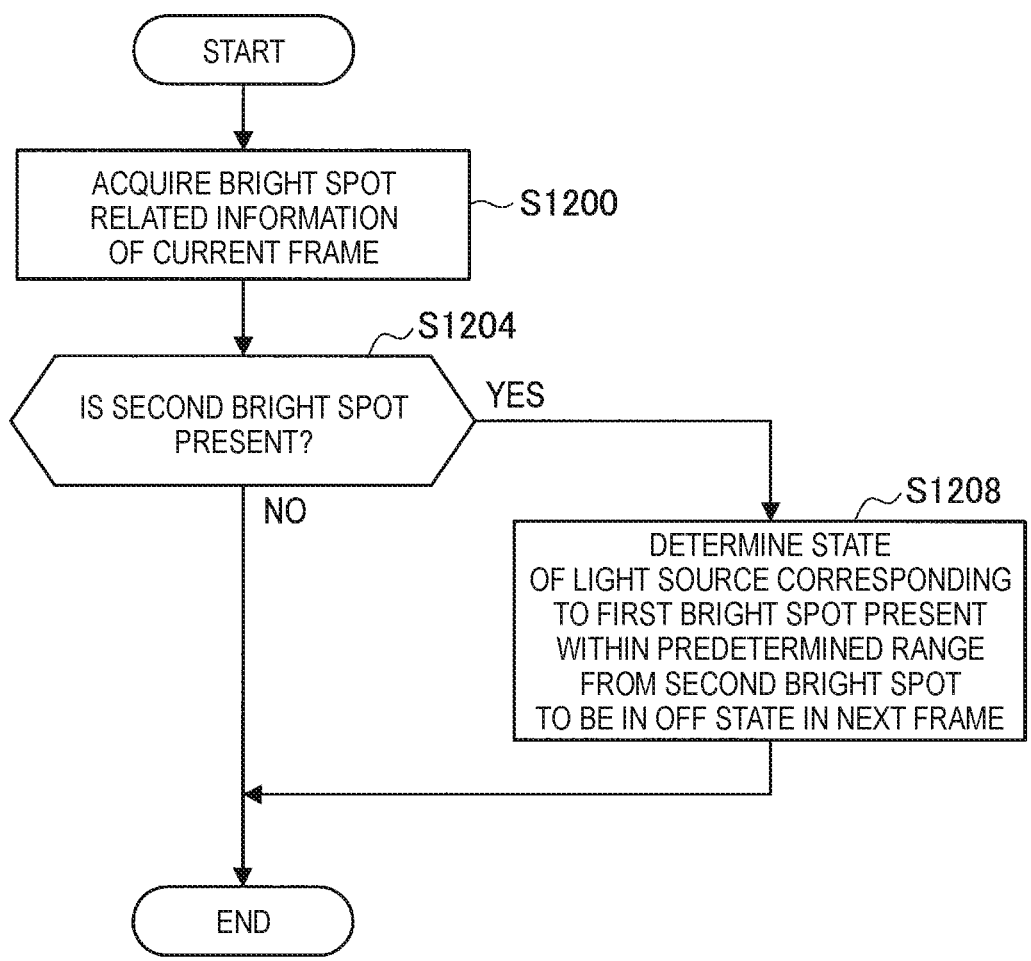
FIG. 9 is a flowchart illustrating the change processing of the blinking pattern of the light source based on the distribution state of the bright spots according to an embodiment of the present disclosure.

Next, a processing flow of the change of the blinking pattern of the light source 101 based on the distribution state of the bright spots 15 will be described with reference to FIG. 9. FIG. 9 is a flowchart illustrating the change processing of the blinking pattern of the light source 101 based on the distribution state of the bright spots 15 according to an embodiment of the present disclosure. Hereinafter, the bright spot 15 of which the corresponding light source 101 is present will be referred to as a "first bright spot" and the bright spot 15 of Which the corresponding light source 101 is not present will be referred to as a "second bright spot".

First, the light source control unit 102 acquires the bright spot related information including the information regarding the bright spot 15 of the current frame generated by the image processing unit 104 (step S1200). Next, the light source control unit 102 checks the presence or absence of the second bright spot on the basis of the bright spot related information and the bright spot light source correspondence information generated by the collation unit 105. Specifically, the light source control unit 102 checks the presence or absence of a bright spot 15 that is not included in the bright spot light source correspondence information among the bright spots 15 generated in the current frame included in the bright spot related information.

In a case in which the second bright spot is present in the current frame (step S1204/Yes), the light source control unit 102 calculates the first spot present within a predetermined distance from the position of the second bright spot and determines the state of the light source 101 corresponding to the calculated first bright spot to be in the off state in the next frame (step S1208). Here, in a case in which the blinking pattern used by the light source control unit 102 sets the state of the light source 101 corresponding to the first bright spot to be in the on state in the next frame, the light source control unit 102 changes the blinking pattern to the blinking pattern that sets the state of the light source 101 corresponding to the first bright spot to be in the off state in the next frame.

It is possible to set the state of the light source 101 corresponding to the first spot in which the second bright spots are distributed to be in the off state in the next frame, by setting the distance between the second bright spot and the first bright spot in which the second bright spots are distributed in the "predetermined distance" described above. Therefore, since it is possible to prevent the generation of the second bright spot in the next frame, it is possible to improve the accuracy of the association between the bright spot 15 and the light source 101. In addition, since only the light source 101 corresponding to the first bright spot is set to be in the on state, the light source 101 that is a candidate for the association is limited and it is easy to associate the bright spot 15 and the light source 101 with each other.

[3.4. Change of Blinking Pattern of Light Source Based on Eye Related Information]

Figure 10:
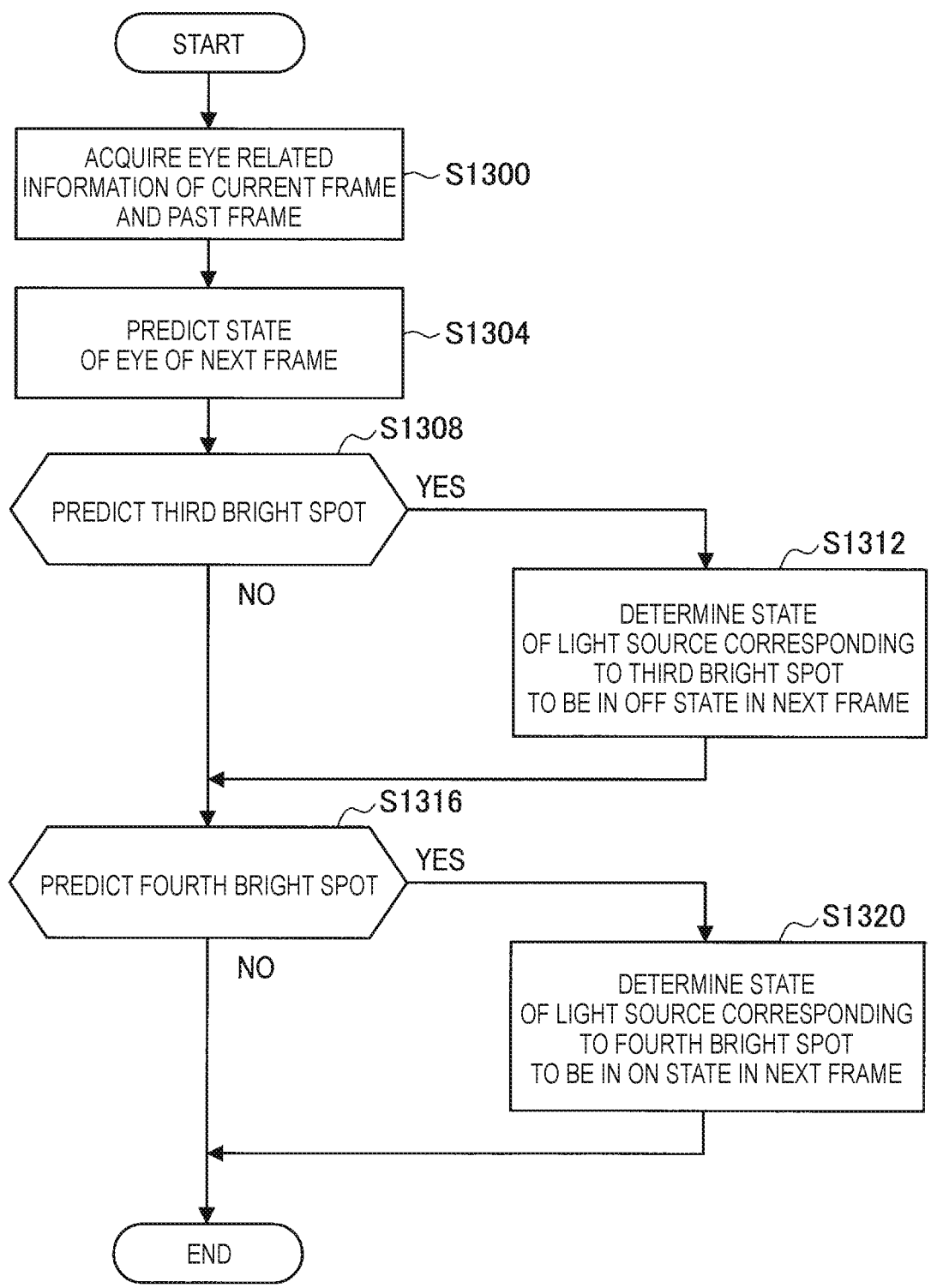
FIG. 10 is a flowchart illustrating the change processing of the blinking pattern of the light source based on eye related information according to an embodiment of the present disclosure.

The change of the blinking pattern of the light source 101 based on the distribution state of the bright spots 15 has been described above. Subsequently, an overview of the change of the blinking pattern of the light source 101 based on the eye related information will be described with reference to FIG. 10. FIG. 10 is a flowchart illustrating change processing of the blinking pattern of the light source 101 based on the eye related information according to an embodiment of the present disclosure.

This method is a method of setting the state of the light source 101 where it is predicted that the bright spot 15 is not generated on the cornea to be in the off state and setting the state of the light source 101 where it is predicted that the bright spot 15 is generated on the cornea to be in the on state, on the basis of the state of the eye (the outer corner of the eye, the inner corner of the eye, the eyelid, the eyelash, and the like).

First, the light source control unit 102 acquires the eye related information including the information regarding the state of the eye (the outer corner of the eye, the inner corner of the eye, the eyelid, the eyelash, and the like) in the current frame and the past frame generated by the image processing unit 104 (step S1300). In addition, the light source control unit 102 predicts the state of the eye in the next frame on the basis of the eye related information (step S1304). Specifically, the light source control unit 102 predicts a region where the cornea 11 is exposed in the next frame by applying three-dimensional coordinate information of the outer corner of the eye, the inner corner of the eye, the eyelid, the eyelash, and the like included in the eye related information to the polynomial function.

Next, the light source control unit 102 checks the presence of absence of a bright spot 15 (hereinafter, referred to as a "third bright spot") that is not positioned in the region where it is predicted that the cornea 11 is exposed in the next frame among the bright spots 15 included in the bright spot light source correspondence information provided from the collation unit 105. In a case in which the third bright spot is present (step S1308/Yes), the light source control unit 102 determines the state of the light source 101 corresponding to the third bright spot to be in the off state in the next frame (step S1312). Here, in a case in which the blinking pattern used by the light source control unit 102 sets the state of the light source 101 corresponding to the third bright spot to be in the on state in the next frame, the light source control unit 102 changes the blinking pattern to the blinking pattern that sets the state of the light source 101 corresponding to the third bright spot to be the off state in the next frame.

Next, the light source control unit 102 checks the presence of absence of a bright spot 15 (hereinafter, referred to as a "fourth bright spot") that is positioned in the region where it is predicted that the cornea 11 is exposed in the next frame among the bright spots 15 included in the bright spot light source correspondence information provided from the collation unit 105 (step S1316). In a case in which the fourth bright spot is present (step S1316/Yes), the light source control unit 102 determines the state of the light source 101 corresponding to the fourth bright spot to be in the on state in the next frame (step S1320). Here, in a case in which the blinking pattern used by the light source control unit 102 does not set the state of the light source 101 corresponding to the fourth bright spot to be in the on state in the next frame, the light source control unit 102 changes the blinking pattern to the blinking pattern that sets the state of the light source 101 corresponding to the fourth bright spot to be the on state in the next frame.

Since it is possible to prevent the generation of the bright spot 15 that is not appearing on the cornea 11 and it is possible to cause the bright spot 15 that is appearing on the cornea 11 to be generated even in a case in which the region of the cornea 11 exposed by the movement of the eye changes, by the method described above, it is possible to improve the accuracy of the association between the bright spot 15 and the light source 101, in addition, since only the light source 101 corresponding to the bright spot 15 appearing on the cornea 11 is set to be in the on state, the light source 101 that is a candidate for the association is limited and it is easy to associate the bright spot 15 and the light source 101 with each other.

[3.5. Change of Blinking Pattern of Light Source Based on Statistical Information]

Next, an overview of the change of the blinking pattern of the light source 101 based on the statistical information will be described. This method is a method of changing the blinking pattern so as to generate the bright spot 15 with higher accuracy of the association between the bright spot 15 and the light source 101, on the basis of the statistical information. Here, the statistical information is information indicating a relationship between the imaging result and the accuracy of the bright spot light source correspondence information obtained by an experiment or the like in advance. Specifically, the statistical information is information indicating the relationship between various kinds of information (the information regarding the pupil position, the bright spot position, the eyeball center position, and the eyeball shape) obtained by analyzing the captured image 14 and the accuracy of the association between the bright spot 15 and the light source 101 performed by using the captured image 14. It is possible to ascertain of the state of the eye (including the bright spot 15) in which the accuracy of the association between the bright spot 15 and the light source 101 is relatively high or the state of the eye (including the bright spot 15) in which the accuracy of the association between the bright spot 15 and the light source 101 is relatively low, by the statistical information.

Figure 11:
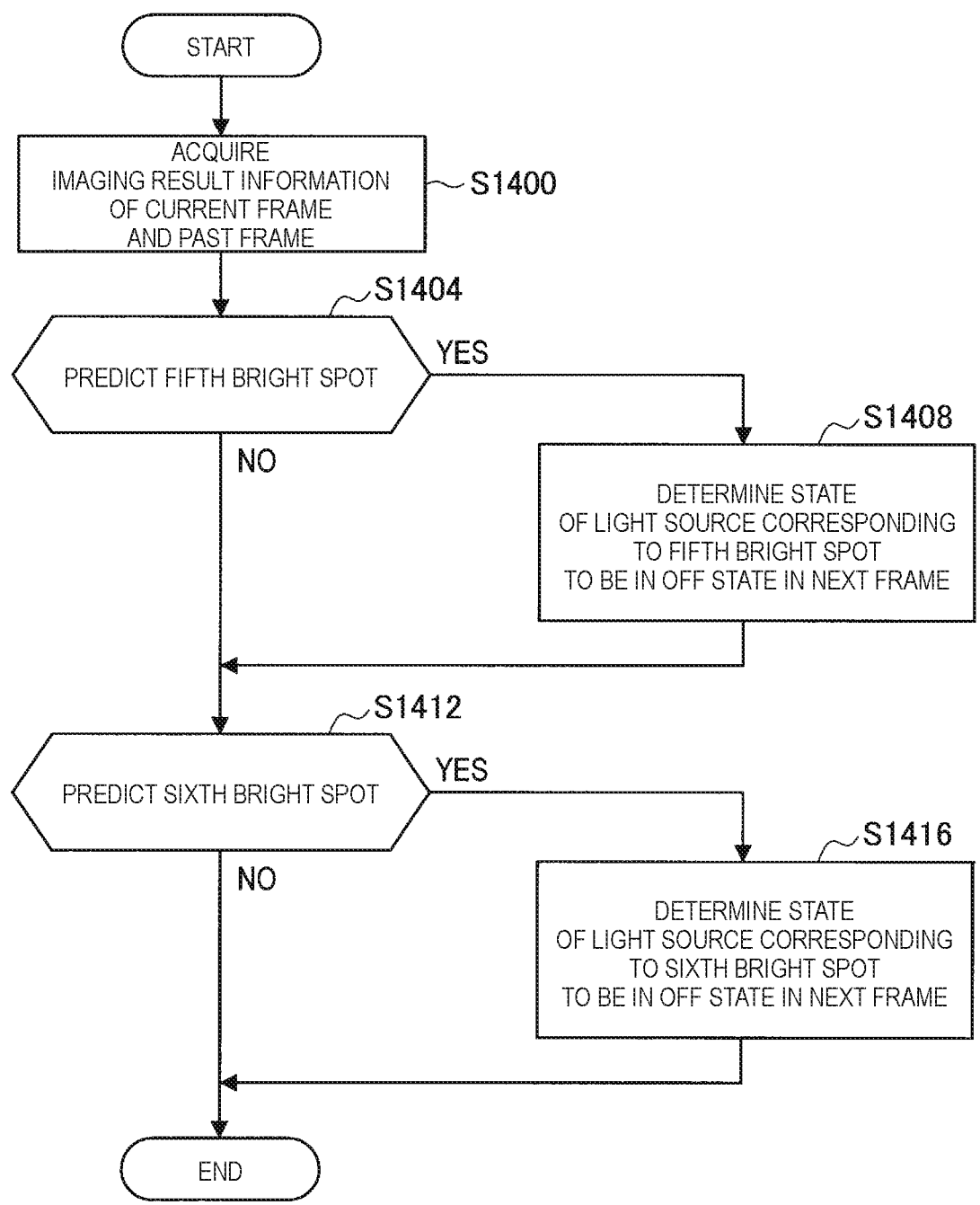
FIG. 11 is a flowchart illustrating the change processing of the blinking pattern of the light source based on statistical information according to an embodiment of the present disclosure.

Next, a processing flow of the change of the blinking pattern of the light source 101 based on the statistical information will be described. FIG. 11 is a flowchart illustrating the change processing of the blinking pattern of the light source 101 based on the statistical information according to an embodiment of the present disclosure. Hereinafter, a bright spot 15 of which the association between the bright spot 15 and the light source 101 is statistically higher than a predetermined threshold value on the basis of the statistical information will be referred to as a "fifth bright spot". In addition, hereinafter, a bright spot 15 of which the association between the bright spot 15 and the light source 101 is statistically lower than the predetermined threshold value on the basis of the statistical information will be referred to as a "sixth bright spot".

First, the light source control unit 102 acquires the imaging analysis information of the current frame and the past frame (step S1400). The imaging analysis information of the past frame may be suitably omitted. Next, the light source control unit 102 predicts the presence or absence of the fifth bright spot (step S1404). In a case in which it is able to be predicted that the fifth bright spot is generated (step S1404/Yes), the light source control unit 102 determines the state of the light source 101 corresponding to the fifth bright spot to be in the on state in the next frame (step S1408). Here, in a case in which the blinking pattern used by the light source control unit 102 does not set the state of the light source 101 corresponding to the fifth bright spot to be in the on state in the next frame, the light source control unit 102 changes the blinking pattern to the blinking pattern that sets the state of the light source 101 corresponding to the fifth bright spot to be the on state in the next frame.

Next, the light source control unit 102 predicts the presence or absence of the sixth bright spot (step S1412). In a case in which it is able to be predicted that the sixth bright spot is generated (step S1412/Yes), the light source control unit 102 determines the state of the light source 101 corresponding to the sixth bright spot to be in the off state in the next frame (step S1416). Here, in a case in which the blinking pattern used by the light source control unit 102 sets the state of the light source 101 corresponding to the sixth bright spot to be in the on state in the next frame, the light source control unit 102 changes the blinking pattern to the blinking pattern that sets the state of the light source 101 corresponding to the sixth bright spot to be the off state in the next frame.

The bright spot 15 having statistically high accuracy of the association between the bright spot 15 and the light source 101 is generated according to the pupil position, the bright spot position, the eyeball center position, the eyeball shape, and the like obtained from the captured image 14, by the method described above, and thus it is possible to prevent the generation of the bright spot 15 having the statistically low accuracy. Therefore, it is possible to improve the accuracy of the association between the bright spot 15 and the light source 101. In addition, since only the light source 101 corresponding to the bright spot 15 of which the accuracy of the association between the bright spot 15 and the light source 101 is higher than the predetermined threshold value is set to be in the on state, the light source 101 that is a candidate for the association is limited and it is easy to associate the bright spot 15 and the light source 101 with each other.

[3.6. Summary of Embodiment of the Present Disclosure]

The example in which the blinking pattern of the light source 101 is changed in an embodiment of the present disclosure has been described above. As described above, according to an embodiment of the present disclosure, it is possible to dynamically change the blinking pattern of the light source 101 on the basis of the imaging result. Therefore, since it is possible to improve the accuracy of the association between the bright spot 15 and the light source 101, it is possible to improve the accuracy of the line-of-sight estimation. In addition, since the light source 101 that is set to be in the on state is limited, it is possible to easily associate the bright spot 15 and the light source 101 with each other.

<4. Hardware Configuration of Head Mounted Display>

Figure 12:
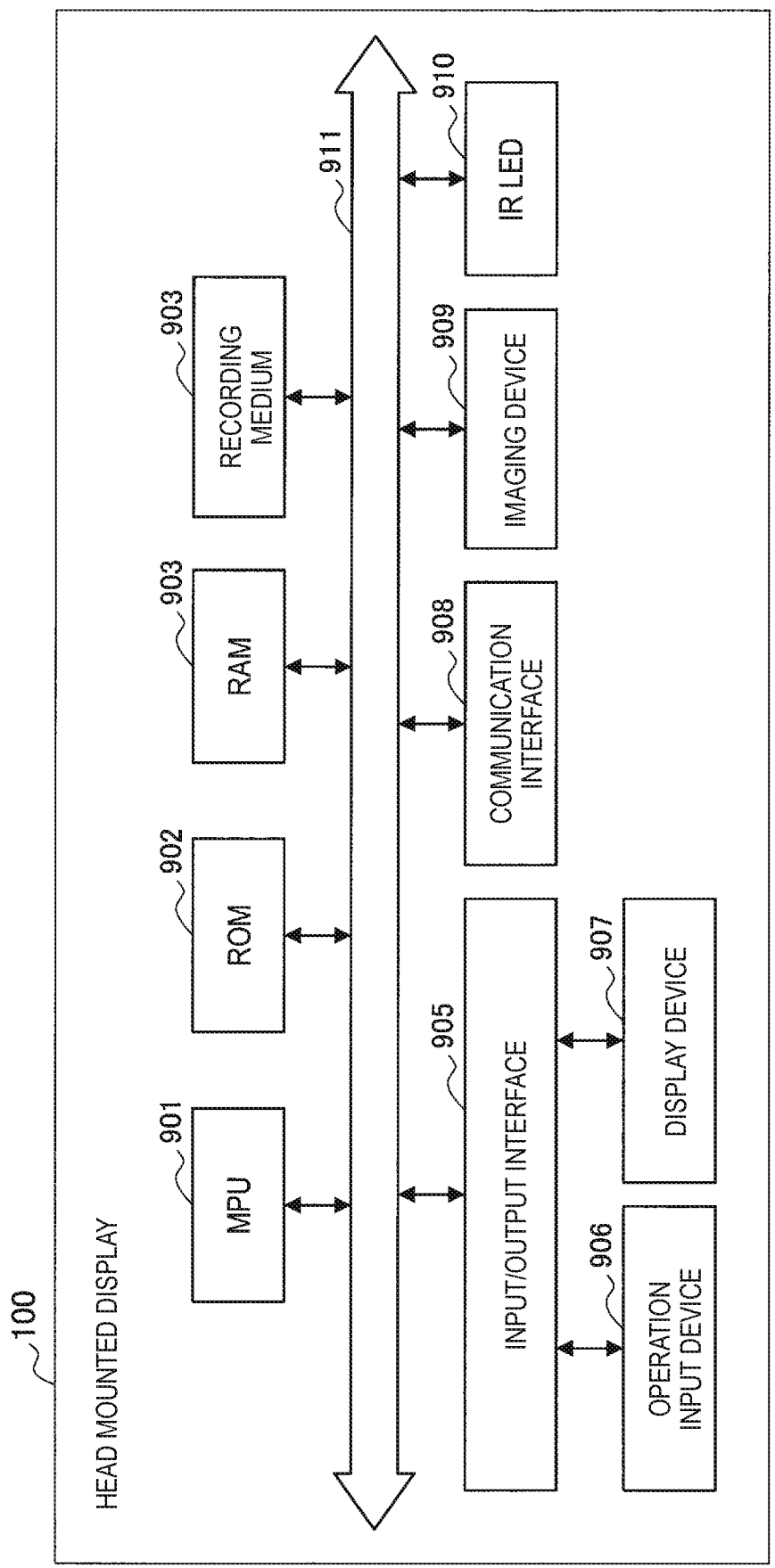
FIG. 12 is a block diagram illustrating a hardware configuration of the head mounted display according to an embodiment of the present disclosure.

FIG. 12 is a block diagram illustrating the hardware configuration of the head mounted display 100 according to an embodiment of the present disclosure. For example, the head mounted display 100 includes an MPU 901, a ROM 902, a RAM 903, a recording medium 904, an input/output interface 905, an operation input device 906, a display device 907, a communication interface 908, an imaging device 909, and an infrared spectroscopy light emitting diode (IR LED) 910. In addition, for example, the head mounted display 100 connects each configuration element with each other by a bus 911 as a data transmission path.

The MPU 901 includes one or more processors or various processing circuits, and has a function of controlling or processing each configuration element included in the head mounted display 100. In addition, for example, the MPU 901 functions as the light source control unit 102, the image processing unit 104, the collation unit 105, the line-of-sight estimation unit 106, and the display control unit 108 in the head mounted display 100.

The ROM 902 functions as the storage unit 109 and stores a program used by the MPU 901, control data such as an operation parameter, or the like. The RAM 903 functions as the storage unit 109 and temporarily stores, for example, a program to be executed by the MPU 901.

The recording medium 904 functions as the storage unit 109, and stores various pieces of data such as data related to information processing method according to the present embodiment such as information related to eyes, image data indicating the captured image, or an application.

An example of the recording medium 904 may include a magnetic recording medium such as a hard disk or a non-volatile memory such as a flash memory. In addition, the recording medium 904 may be detachable from the head mounted display 100.

The input/output interface 905 connects the operation input device 906 and the display device 907 with each other. The operation input device 906 functions as an operation unit (not shown). In addition, the display device 907 functions as the display unit 107. Here, an example of the input/output interface 905 may include a universal serial bus (USB) terminal, a digital visual interface (DVI) terminal, a high-definition multimedia interface (HDMI) (registered trademark) terminal, various processing circuits, or the like.

For example, the operation input device 906 is provided on the head mounted display 100, and is connected with the input/output interface 905 in the head mounted display 100. An example of the operation input device 906 may include a button, a direction key, a rotary selector such as a jog dial, a combination thereof, or the like.

For example, the display device 907 is provided on the head mounted display 100, and is connected with the input/output interface 905 in the head mounted display 100. An example of the display device 907 may include a liquid crystal display, an organic electro-luminescence display, an organic light emitting diode display (OLED), or the like.

In addition, it is needless to say that the input/output interface 905 is able to be connected to an external device such as an operation input device (for example, a keyboard, a mouse, or the like), a display device, or an imaging device as an external device of the head mounted display 100. In addition, for example, the display device 907 may be a device that is able to perform a display and a user operation such as a touch device.

The communication interface 908 is communication means included in the head mounted display 100. The communication interface 908 functions as a communication unit (not shown) for performing wireless or wired communication with an external device (or an external apparatus) such as an external imaging device, an external display device, an external device attached to a head of the user according to the present embodiment to be used through a network (or directly).

An example of the communication interface 908 includes a communication antenna and radio frequency (RF) circuit (wireless communication), an IEEE802.15.1 port and transmission and reception circuit (wireless communication), an IEEE802.11 port and transmission and reception circuit (wireless communication), a local area network (LAN) terminal and transmission and reception circuit (wired communication), or the like. In addition, the communication unit (not shown) may be a configuration corresponding to an arbitrary standard capable of performing communication such as a universal serial bus (USB) terminal and transmission and reception circuit, or an arbitrary configuration capable of communicating with an external device through a network.

In addition, an example of the network according to the present embodiment may include a wired network such as a LAN or a wide area network (WAN), a wireless network such as a wireless wide area network (WWAN) through a wireless local area network (WLAN) or a base station, or the Internet using a communication protocol such as a transmission control protocolsurasshuInternet Protocol (TCP/IP).

The imaging device 909 is imaging means included in the head mounted display 100 and functions as the imaging unit 103 that generates the captured image by imaging. For example, the imaging device 909 is an imaging element such as a charge-coupled device (CCD) image sensor or a complementary MOS (CMOS) image sensor. The imaging device 909 acquires an image (the captured image) according to incident light on a light receiving surface by outputting a signal having intensity according to an amount of light received for each pixel including the light receiving surface. In addition, for example, the imaging device 909 is provided at a position where it is possible to image the eye with which the light from the light source 101 such as an IR LED is irradiated.

In a case in which the imaging device 909 is provided, in the head mounted display 100, for example, it is possible to performing the processing related to the imaging processing method according to the present embodiment on the basis of the captured image generated by the imaging in the imaging device 909.

For example, the imaging device 909 includes a lens or an imaging element and a signal processing circuit. The lens or the imaging element includes, for example, a lens of an optical system and an image sensor using a plurality of imaging elements such as a complementary metal oxide semiconductor (CMOS).

For example, the signal processing circuit includes an automatic gain control (AGC) circuit or an analog to digital converter (ADC) and converts an analog signal generated by the imaging element to a digital signal (image data). In addition, the signal processing circuit performs various kinds of processing related to, for example, a RAW development. In addition, for example, the signal processing circuit may perform various kinds of signal processing such as white balance correction processing, color tone correction processing, gamma correction processing, YCbCr conversion processing, or edge emphasis processing.

The IR LED 910 is the light source 101 included in the head mounted display 100 and includes a plurality of IR LEDs. For example, the IR LED 910 is provided at the position where the eye of the user is irradiated with the light. Since the light source 101 is a device that emits light other than light of a visible light band as the IR LED 910, even though the eyeball 10 of the user is irradiated with the light from the light source 101, a view of the user is not disturbed. In addition, as described above, the light source 101 included in the head mounted display 100 is not limited to the IR LED, and various optical elements may be applied to the light source 101 as long as the various optical elements are optical elements that emit light.

For example, the head mounted display 100 performs the processing related to the information processing method according to the present embodiment by a configuration shown in FIG. 12. In addition, the hardware configuration of the head mounted display 100 according to the present embodiment is not limited to the configuration shown in FIG. 12.

For example, the head mounted display 100 may not include one or both of the imaging device 909 and the IR LED 910.

In addition, for example, in a case in which the head mounted display 100 is configured to perform processing in a stand-alone state, the head mounted display 100 may not include the communication interface 908. In addition, the head mounted display 100 may not include the recording medium 904, the operation input device 906, or the display device 907.

In addition, the configuration of the head mounted display 100 according to an embodiment of the present disclosure is not limited to the configuration shown in FIG. 3.

For example, a part of the configuration of the head mounted display 100 according to an embodiment of the present disclosure may be provided at the outside.

For example, in a case in which the analysis processing is performed on the captured image information in the external device and the processing is performed using the processing result of the external device, the head mounted display 100 may not include the image processing unit 104.

In addition, in a case in which the processing of associating the light source 101 and the bright spot 15 with each other is performed in the external device and the processing is performed using the processing result of the external device, the head mounted display 100 may not include the collation unit 105.

In addition, in a case in Which the processing of the line-of-sight estimation is performed in the external device and the processing is performed using the processing result of the external device, the head mounted display 100 may not include the line-of-sight estimation unit 106.

In addition, in a case in which the processing of storing various pieces of information is performed in the external device and the processing is performed using the information stored in the external device, the head mounted display 100 may not include the storage unit 109.

The head mounted display 100 has been described above as an embodiment of the present disclosure, but the embodiment of the present disclosure is not limited to such an embodiment. For example, the embodiment of the present disclosure is able to be applied to various devices capable of processing an image, such as an information processing apparatus such as a personal computer (PC) or a server, a communication device such as a mobile phone or a smartphone, or a tablet type device. In addition, for example, the present embodiment is also able to be applied to one or more integrated circuits (ICs) that are able to be incorporated in the above-described devices.

In addition, for example, the present disclosure may be applied to a system including one or more devices on the premise of connection to a network (or communication between devices) such as a cloud computing. That is, for example, the head mounted display 100 according to an embodiment of the present disclosure described above is also able to be realized as an information processing system including a plurality of devices.

<5. Supplement>

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, the light source control unit 102 may control the light source 101 so that the state of the light source 101 corresponding to a region where the accuracy of the line-of-sight estimation on the display unit 107 is desired to be improved in the application displayed on the display unit 107 is set to be in the on state. For example, in a case in which a button of a region where buttons are densely is selected by a pointer operated by the line-of-sight estimation, it is possible to relatively improve the accuracy of the line-of-sight estimation for the region than the accuracy of the line-of-sight estimation for other regions, by setting the state of the light source 101 corresponding to the region direction to be in the on state.

In addition, the light source control unit 102 may control the light source 101 so that a predetermined number of bright spots 15 sufficient for the line-of-sight estimation are generated on the cornea in all frames or at a frequency equal to or greater than a predetermined threshold value.

In addition, of course, the light source control unit 102 may control the light source 101 on the basis of a blinking pattern that is set in advance without changing the blinking pattern.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)
An information processing apparatus including:
a light source control unit configured to control each of light sources constituting a plurality of light sources that irradiate an eye with light; and
an image acquisition unit configured to acquire a captured image of the eye including a bright spot that is a reflection point of the light,
in which the light source control unit controls blinking of each of the light sources on a basis of the captured image of the eye.

(2)
The information processing apparatus according to (1), in which the light source control unit controls the blinking of each of the light sources on a basis of bright spot light source correspondence information that is information in which the captured bright spot and each of the light sources are associated with each other and imaging analysis information that is information regarding an imaging result of the eye.

(3)
The information processing apparatus according to (2), in which the light source control unit determines a light source to be in an on state in a frame in which imaging processing is performed after a frame during the imaging processing, on a basis of the bright spot light source correspondence information and the imaging analysis information before the frame during the imaging processing.

(4)
The information processing apparatus according to (3), in which the light source control unit determines the light source to be in the on state in the frame in which the imaging processing is performed next to the frame during the imaging processing, on the basis of the bright spot light source correspondence information and the imaging analysis information before the frame during the imaging processing.

(5)
The information processing apparatus according to any one of (2) to (4), in which the light source control unit determines a light source to be in an on state or an off state on a basis of a blinking pattern in which a pattern for setting each of the light sources to be in the on state or the off state is defined, and changes the blinking pattern on the basis of the bright spot light source correspondence information and the imaging analysis information.

(6)
The information processing apparatus according to any one of (2) to (5), in which the imaging analysis information is position information regarding a pupil.

(7)
The information processing apparatus according to (6), in which the light source control unit determines a light source to be in an on state on a basis of a position of the pupil or a pupil center predicted by the position information regarding the pupil.

(8)
The information processing apparatus according to (7), in which the light source control unit sets a light source associated with a predetermined number of bright spots of which distances to the predicted position of the pupil or the pupil center are relatively close, among bright spots included in the bright spot light source correspondence information, to be in the on state.

(9)

The information processing apparatus according to any one of (2) to (5), in which the imaging analysis information is position information of a bright spot of which an associated light source is not present.

(10)

The information processing apparatus according to (9), in which the light source control unit sets a light source associated with a bright spot of which a distance to the bright spot of which an associated light source is not present is within a predetermined range, among bright spots included in the bright spot light source correspondence information, to be in an off state.

(11)

The information processing apparatus according to any one of (2) to (5), in which the imaging analysis information is eye related information that is information regarding a state of an imaged outer corner of eye, inner corner of eye, or eyelid.

(12)

The information processing apparatus according to (11), in which, in a case in which it is predicted that the bright spot is not generated on a cornea on a basis of the eye related information, the light source control unit sets a light source associated with the bright spot to be in an off state.

(13)

The information processing apparatus according to (11) or (12), in which, in a case in which it is predicted that the bright spot is generated on a cornea on a basis of the eye related information, the light source control unit sets a light source associated with the bright spot to be in an on state.

(14)

The information processing apparatus according to any one of (2) to (5), in which the light source control unit determines a light source to be in an on state on a basis of statistical information regarding an accuracy of the bright spot light source correspondence information.

(15)

The information processing apparatus according to (14), in which the light source control unit sets a light source associated with a bright spot of which the accuracy of the bright spot light source correspondence information is higher than a predetermined threshold value to be in the on state on the basis of the statistical information.

(16)

The information processing apparatus according to (14) or (15), in which the light source control unit sets a light source associated with a bright spot of which the accuracy of the bright spot light source correspondence information is lower than a predetermined threshold value to be in an off state on the basis of the statistical information.

(17)

A computer-readable recording medium having a program for realizing functions recorded thereon, the functions including:
  a light source control function of controlling each of light sources constituting a plurality of light sources that irradiate an eye with light;
  an image acquisition function of acquiring a captured image of the eye including a bright spot that is a reflection point of the light; and
  a function of controlling blinking of each of the light sources on a basis of the captured image of the eye.

(18)

An information processing method including:
  controlling each of light sources constituting a plurality of light sources that irradiate an eye with light; and
  acquiring a captured image of the eye including a bright spot that is a reflection point of the light,
  in which blinking of each of the light sources is controlled on a basis of the captured image of the eye.

REFERENCE SIGNS LIST 100 head mounted display
101 light source
102 light source control unit
103 imaging unit
104 image processing unit
105 collation unit
106 line-of-sight estimation unit
107 display unit
108 display control unit
109 storage unit

The invention claimed is:

1. An information processing apparatus comprising:
  a light source control unit configured to control each of light sources constituting a plurality of light sources that irradiate an eye with light; and
  an image acquisition unit configured to acquire a current frame of a captured image of the eye including a bright spot that is a reflection point of the light,
  wherein the light source control unit controls blinking of each of the light sources on a basis of imaging processing performed on the current frame of the captured image of the eye,
  wherein the light source control unit controls the blinking of each of the light sources on a basis of bright spot light source correspondence information in which the captured bright spot and each of the light sources are associated with each other and imaging analysis information that is information regarding an imaging result of the eye,
  wherein the light source control unit determines a light source to be in an on state in a next frame in which imaging processing is performed after the imaging processing is performed on the current frame, on a basis of the bright spot light source correspondence information and the imaging analysis information obtained before imaging the current frame, and p1 wherein the light source control unit and the image acquisition unit are each implemented via at least one processor.

2. The information processing apparatus according to claim 1, wherein the light source control unit determines the light source to be in the on state in the next frame in which the imaging processing is performed next after the imaging processing is performed on the current frame, on the basis of the bright spot light source correspondence information and the imaging analysis information obtained before imaging the current frame during the imaging processing.

3. The information processing apparatus according to claim 1, wherein the light source control unit determines a light source to be in an on state or an off state on a basis of a blinking pattern in which a pattern for setting each of the light sources to be in the on state or the off state is defined, and changes the blinking pattern on the basis of the bright spot light source correspondence information and the imaging analysis information.

4. The information processing apparatus according to claim 1, wherein the imaging analysis information is position information regarding a pupil.

5. The information processing apparatus according to claim 4, wherein the light source control unit determines a light source to be in an on state on a basis of a position of the pupil or a pupil center predicted by the position information regarding the pupil.

6. The information processing apparatus according to claim 5, wherein the light source control unit sets a light source associated with a predetermined number of bright spots of which distances to the predicted position of the pupil or the pupil center are relatively close, among bright spots included in the bright spot light source correspondence information, to be in the on state.

7. The information processing apparatus according to claim 1, wherein the imaging analysis information is position information of a bright spot of which an associated light source is not present.

8. The information processing apparatus according to claim 7, wherein the light source control unit sets a light source associated with a bright spot of which a distance to the bright spot of which an associated light source is not present is within a predetermined range, among bright spots included in the bright spot light source correspondence information, to be in an off state.

9. The information processing apparatus according to claim 1, wherein the imaging analysis information is eye related information that is information regarding a state of an imaged outer corner of eye, inner corner of eye, or eyelid.

10. The information processing apparatus according to claim 9, wherein, in a case in which it is predicted that the bright spot is not generated on a cornea on a basis of the eye related information, the light source control unit sets a light source associated with the bright spot to be in an off state.

11. The information processing apparatus according to claim 9, wherein, in a case in which it is predicted that the bright spot is generated on a cornea on a basis of the eye related information, the light source control unit sets a light source associated with the bright spot to be in an on state.

12. The information processing apparatus according to claim 1, wherein the light source control unit determines a light source to be in an on state on a basis of statistical information regarding an accuracy of the bright spot light source correspondence information.

13. The information processing apparatus according to claim 12, wherein the light source control unit sets a light source associated with a bright spot of which the accuracy of the bright spot light source correspondence information is higher than a predetermined threshold value to be in the on state on the basis of the statistical information.

14. The information processing apparatus according to claim 12, wherein the light source control unit sets a light source associated with a bright spot of which the accuracy of the bright spot light source correspondence information is lower than a predetermined threshold value to be in an off state on the basis of the statistical information.

15. A non-transitory computer-readable medium having embodied thereon a program, which when executed by a computer causes the computer to execute a method, the method comprising:
controlling each of light sources constituting a plurality of light sources that irradiate an eye with light;
acquiring a current frame of a captured image of the eye including a bright spot that is a reflection point of the light;
controlling blinking of each of the light sources on a basis of imaging processing performed on the current frame of the captured image of the eye,
wherein the controlling of the blinking of each of the light sources is based on bright spot light source correspondence information in which the captured bright spot and each of the light sources are associated with each other and imaging analysis information that is information regarding an imaging result of the eye; and
determining a light source to be in an on state in a next frame in which imaging processing is performed after the imaging processing is performed on the current frame, on a basis of the bright spot light source correspondence information and the imaging analysis information obtained before imaging the current frame.

16. An information processing method comprising:
controlling each of light sources constituting a plurality of light sources that irradiate an eye with light;
acquiring a current frame of a captured image of the eye including a bright spot that is a reflection point of the light;
controlling blinking of each of the light sources on a basis of imaging processing performed on the current frame of the captured image of the eye,
wherein the controlling of the blinking of each of the light sources is based on bright spot light source correspondence information in which the captured bright spot and each of the light sources are associated with each other and imaging analysis information that is information regarding an imaging result of the eye; and
determining a light source to be in an on state in a next frame in which imaging processing is performed after the imaging processing is performed on the current frame, on a basis of the bright spot light source correspondence information and the imaging analysis information obtained before imaging the current frame.

* * * * *